United States Patent
Berger et al.

(10) Patent No.: US 8,525,059 B2
(45) Date of Patent: Sep. 3, 2013

(54) HANDPIECE FINGER SWITCH FOR ACTUATION OF HANDHELD MEDICAL INSTRUMENTATION

(75) Inventors: John Berger, Laguna Niguel, CA (US); Dmitri Boutoussov, Dana Point, CA (US)

(73) Assignee: Biolase, Inc., Irvine, CA (US)

(*) Notice: Subject to any disclaimer, the term of this patent is extended or adjusted under 35 U.S.C. 154(b) by 281 days.

(21) Appl. No.: 12/985,959

(22) Filed: Jan. 6, 2011

(65) Prior Publication Data

US 2011/0165535 A1 Jul. 7, 2011

Related U.S. Application Data

(60) Provisional application No. 61/292,697, filed on Jan. 6, 2010.

(51) Int. Cl.
*H01H 1/10* (2006.01)
(52) U.S. Cl.
USPC ............................................. 200/512; 607/89
(58) Field of Classification Search
USPC ........................................... 200/512; 607/89
See application file for complete search history.

(56) References Cited

U.S. PATENT DOCUMENTS

| | | | |
|---|---|---|---|
| 4,478,217 A * | 10/1984 | Shimada et al. | 606/13 |
| 4,492,832 A | 1/1985 | Taylor | |
| 5,451,735 A * | 9/1995 | Worthington et al. | 200/505 |
| 6,500,144 B1 | 12/2002 | Russell et al. | |
| 8,242,398 B2 * | 8/2012 | Young et al. | 200/332.2 |
| 2008/0108869 A1 | 5/2008 | Sanders et al. | |
| 2008/0203280 A1 | 8/2008 | Rizoiu | |

FOREIGN PATENT DOCUMENTS

| | | |
|---|---|---|
| DE | 2460481 | 6/1976 |
| GB | 2450239 | 12/2008 |

OTHER PUBLICATIONS

International Search Report and Written Opinion, PCT/US2011/020394, mailed Mar. 7, 2011.
Supplementary European Search Report dated Jun. 25, 2013 from related/corresponding EP Appl No. 11732151.3 (base on PCT/US11/20394).

* cited by examiner

*Primary Examiner* — Vanessa Girardi
(74) *Attorney, Agent, or Firm* — Jones Day

(57) ABSTRACT

A handpiece for a medical instrumentation device is formed with manually deformable ribs on an outer sleeve. The ribs align with conductive surfaces inside the handpiece that make contact with an internal flexible electronic circuit to activate the device when force is applied to the ribs. Removing the force deactivates the device.

4 Claims, 2 Drawing Sheets

HANDPIECE FINGER SWITCH FOR ACTUATION OF HANDHELD MEDICAL INSTRUMENTATION

CROSS-REFERENCE TO RELATED APPLICATIONS

This application claims the benefit of Prov. App. 61/292,697, filed on Jan. 6, 2010 and entitled HANDPIECES FINGER SWITCH FOR LASER ACTUATION, the entire contents of which are hereby incorporated by reference.

BACKGROUND OF THE INVENTION

1. Field of the Invention

The present invention relates generally to handheld medical instrumentation and, more particularly, to apparatus for facilitating actuation of handheld medical instrumentation.

2. Description of Related Art

Typical methods of actuating medical handtools and/or laser handpieces may prevent or at least impede effective operation or optimal utilization of the instrumentation. For example, actuation of medical devices (e.g., cutters) in some situations such as in the context of dental laser procedures, e.g., operating within an oral cavity which can be particularly complex, may pose difficulties in relation to, for instance, a user needing to change her grip on a device and/or re-position the device without losing an ability to actuate the device.

One known method of actuating a medical device includes disposing a finger switch on a side of the medical device (e.g., laser handpiece). Use of the finger switch, however, may prevent a user from readily changing a grip on the device and/or rotating of such a device while in use, thereby reducing the utility or usability of the device (e.g., laser).

Switches configured for remote-actuation such as in the assemblage of a foot switch may in some environments address this problem, but at the expense of having to add yet further hardware (e.g. a foot pedal) to an array of components (e.g., switches) already in place for related or other applications. As great effort is expended to conserve real estate (e.g., floor and/or counter space) in most surgical/clinical operating rooms, such solutions may be met with reduced acceptance by users in the industry.

A need thus exists in the prior art for a method of actuation of handheld medical instrumentation that allows, for example, for optimal and/or efficient repositioning of the instrumentation while in use without requiring the sacrifice of valuable operating-room space such as required by a foot switch. A further need exists for a method of actuation that permits optimal and/or efficient operation of the instrumentation in complex clinical environments.

SUMMARY OF THE INVENTION

The present invention addresses these needs by providing a handpiece for medical instrumentation, the handpiece exhibiting circumferential geometry. The invention herein disclosed may comprise, according to one embodiment, an inner sleeve, an actuating outer sleeve disposed outside the inner sleeve, and an internal circuit to which contact with the inner sleeve can be controlled by an external force applied to at least a portion of the outer sleeve, the internal circuit being disposed inside the inner sleeve.

According to another embodiment, the outer sleeve may comprise a plurality of ribs having a tactile feel, the ribs being disposed axially on the handpiece, and configured to apply force to a portion of the inner sleeve when the external force is applied to at least one of the ribs.

As an example, the medical instrumentation may comprise a medical laser, and the internal circuit may be a flexible electronic circuit permanently attached over a core of a heat sink of the laser. Further, the inner sleeve may comprise an elastic membrane having a plurality of internal pads painted with conductive ink, the internal pads normally not making contact with the internal circuit. The internal pads may be correspondent with the ribs, and the internal pads may be disposed to make contact with the internal circuit when the external force is applied to at least one of the ribs.

While the apparatus and method has or will be described for the sake of grammatical fluidity with functional explanations, it is to be expressly understood that the claims, unless indicated otherwise, are not to be construed as limited in any way by the construction of "means" or "steps" limitations, but are to be accorded the full scope of the meaning and equivalents of the definition provided by the claims under the judicial doctrine of equivalents.

Any feature or combination of features described or referenced herein are included within the scope of the present invention provided that the features included in any such combination are not mutually inconsistent as will be apparent from the context, this specification, and the knowledge of one skilled in the art. In addition, any feature or combination of features described or referenced may be specifically excluded from any embodiment of the present invention. For purposes of summarizing the present invention, certain aspects, advantages and novel features of the present invention are described or referenced. Of course, it is to be understood that not necessarily all such aspects, advantages or features will be embodied in any particular implementation of the present invention. Additional advantages and aspects of the present invention are apparent in the following detailed description and claims that follow.

DETAILED DESCRIPTION OF THE PRESENTLY PREFERRED EMBODIMENTS

Figure 1:
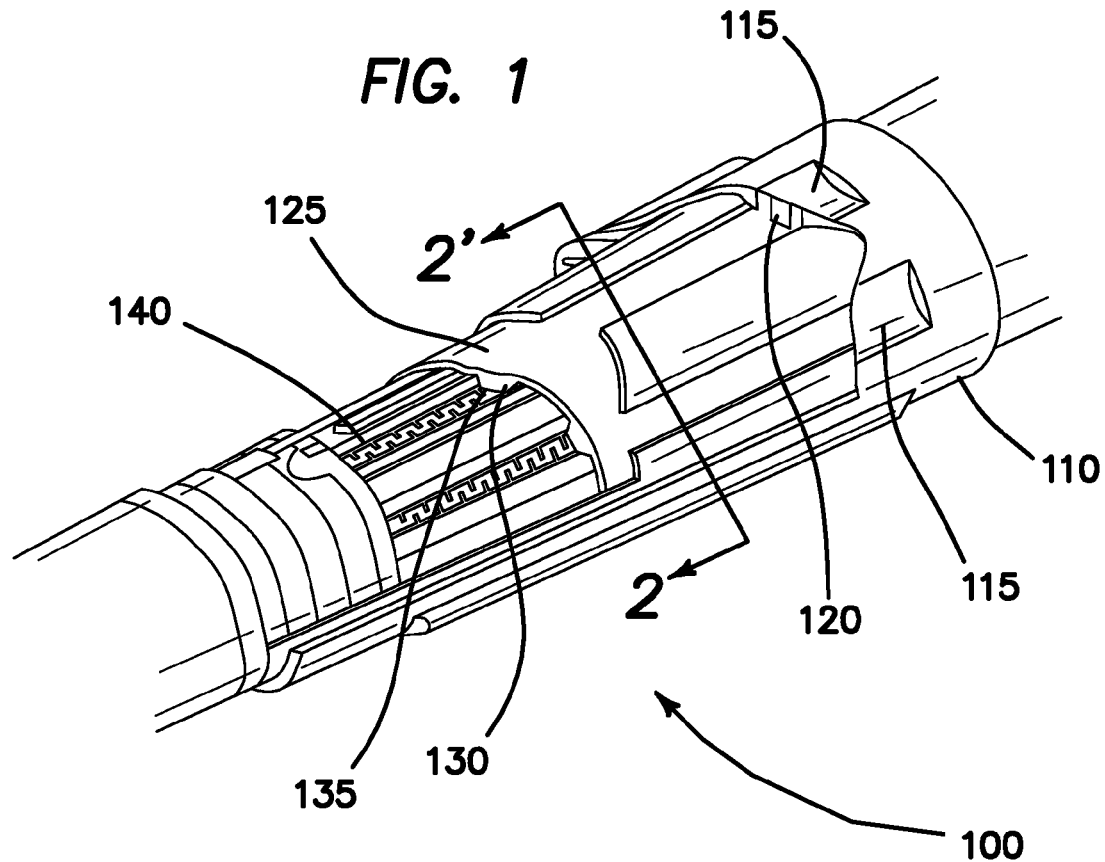
FIG. 1 is a cut-away view of a medical laser handpiece showing components of an embodiment of the present invention.

Embodiments of the invention are now described and illustrated in the accompanying drawings, instances of which are to be interpreted to be to scale in some implementations while in other implementations, for each instance, not. In certain aspects, use of like or the same reference designators in the drawings and description refers to the same, similar or analogous components and/or elements, while according to other implementations the same use should not. According to certain implementations, use of directional terms, such as, top, bottom, left, right, up, down, over, above, below, beneath, rear, and front, are to be construed literally, while in other implementations the same use should not. The present invention may be practiced in conjunction with various devices and techniques that are conventionally used in the art, and only so much of the commonly practiced process steps are included herein as are necessary to provide an understanding of the present invention. The present invention has applicability in the field of medical devices and processes in general. For illustrative purposes, however, the following description pertains to a dental laser device.

Referring more particularly to the drawings, FIG. 1 is a cut-away view of a medical device or instrument, such as a hand-operated cutter or treatment device, which may be embodied as, with reference to the depicted incarnation, a dental laser handpiece 100 elucidating components according to an exemplary construction/assembly of the present invention. The handpiece 100 typically has an axially symmetrical (e.g., nominally cylindrical) shape that may be somewhat tapered and/or that may be sized and shaped to be held and controlled by the hand (e.g., single hand) of a user. The illustrated embodiment comprises an outer sleeve 110 that may include and/or accommodate a plurality of ribs 115 having a tactile feel and/or being disposed axially, i.e., longitudinally or length-wise, on one or more of the outer sleeve 110 and the handpiece 100. According to one exemplary embodiment, the plurality of ribs 115 comprises six ribs spaced at about 60 degrees around the handpiece 100, which ribs 115 can comprise structures extending about a third or half the length of a forefinger and/or structures ranging in length from about one to about two inches. The illustrated embodiment further comprises an inner sleeve 125 that is surrounded by the outer sleeve 110. The inner sleeve 125 may be formed with a plurality of internal pads 130 situated to correspond to part or all of one or more positions of the plurality of ribs 115 of the outer sleeve, the pads 130 extending inward from a remainder of the inner sleeve 125. Inner surfaces 135 of the inner pads 130 may be coated with conducting material, e.g., conducting ink. A flexible electronic circuit 140 may be disposed inward of the inner sleeve 125 and aligned with the plurality of internal pads 130 and the plurality of ribs 115. Each of the plurality of ribs 115 may have formed on an inward surface thereof an actuator plunger 120 disposed to apply a force to the inner sleeve 125 when a force is applied to one of the ribs 115. In this way, force applied to one or more of the ribs 115 may cause an inward surface 135 of at least one of the inner pads 130 to make contact with the flexible electronic circuit 140, which contact may be used to actuate a medical device of which the handpiece 100 may be a part. That is, applying an external force to one or more of the ribs 115 may actuate a medical instrumentation device, e.g., a medical laser. Removing the external force may allow the ribs 115 to assume an at rest state, thereby breaking the contact between the electronic circuit 140 and the inner surface 135 of the inner sleeve 130 and de-actuating the medical instrumentation device.

Figure 2:
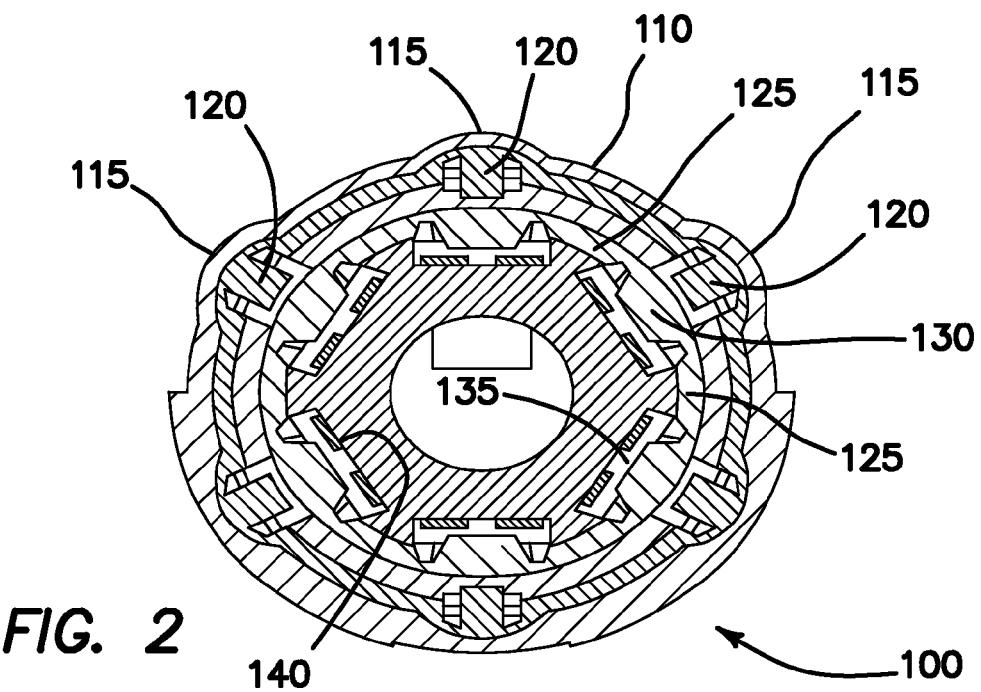
FIG. 2 is a cross-sectional view taken along line 2-2' of the medical laser handpiece of FIG. 1.

FIG. 2 is a cross-sectional view, taken along a line 2-2', of the handpiece 100 of FIG. 1, the handpiece 100 being a part of a medical device, e.g., a medical laser (not shown). FIG. 2 illustrates an actuating outer sleeve 110 with a plurality of ribs 115 formed therein. A flexible electronic circuit 140 is disposed inside the handpiece 100, surrounding and, according to one embodiment, permanently attached over a core of a heat sink of a medical laser, and an inner sleeve 125 is disposed between the ribs and the electronic circuit 140. A plurality of internal pads 130, formed as part of the inner sleeve 125, may be positioned between the ribs 115 and the flexible electronic circuit 140. The ribs 115, which may have a tactile feel, are positioned outside a corresponding plurality of actuator plungers 120 that, in turn, may be positioned outside the plurality of internal pads 130. Inner surfaces 135 of the internal pads 130 may be coated with conducting ink.

Applying an external force to one or more of the plurality of ribs 115 may cause the ribs 115 to deform (and to remain deformed while the external force is applied), thereby causing the actuator plunger 120 to press against the inner sleeve 125. In particular, because of the alignment of the ribs 115 with the internal pads 130, application of the external force may cause the inner surface 135 of the internal pads 130 to make contact with the flexible electronic circuit 140. This contact may initiate actuation, e.g., activation, of the medical device, and removing the external force may deactivate the medical device.

It should be clear that the ribs 115 are normally in the at rest state (or condition) when substantially no force is applied to the ribs 115. The ribs 115 may be configured to deform in response to application of an external force to the ribs 115, which force may result, for example, from simply squeezing, e.g., with a finger, the handpiece 100. When the external (e.g., squeezing) force is removed by, for example, relaxing a grip on the handpiece 100, the ribs 115 may return to the at rest condition, thereby breaking contact between the conducting surface 135 of the inner sleeve and the flexible electronic circuit 140. This squeezing/relaxing action may provide a momentary switching function for a hand-operated medical device or instrument, such as the exemplified handpiece for a medical laser.

Figure 3:
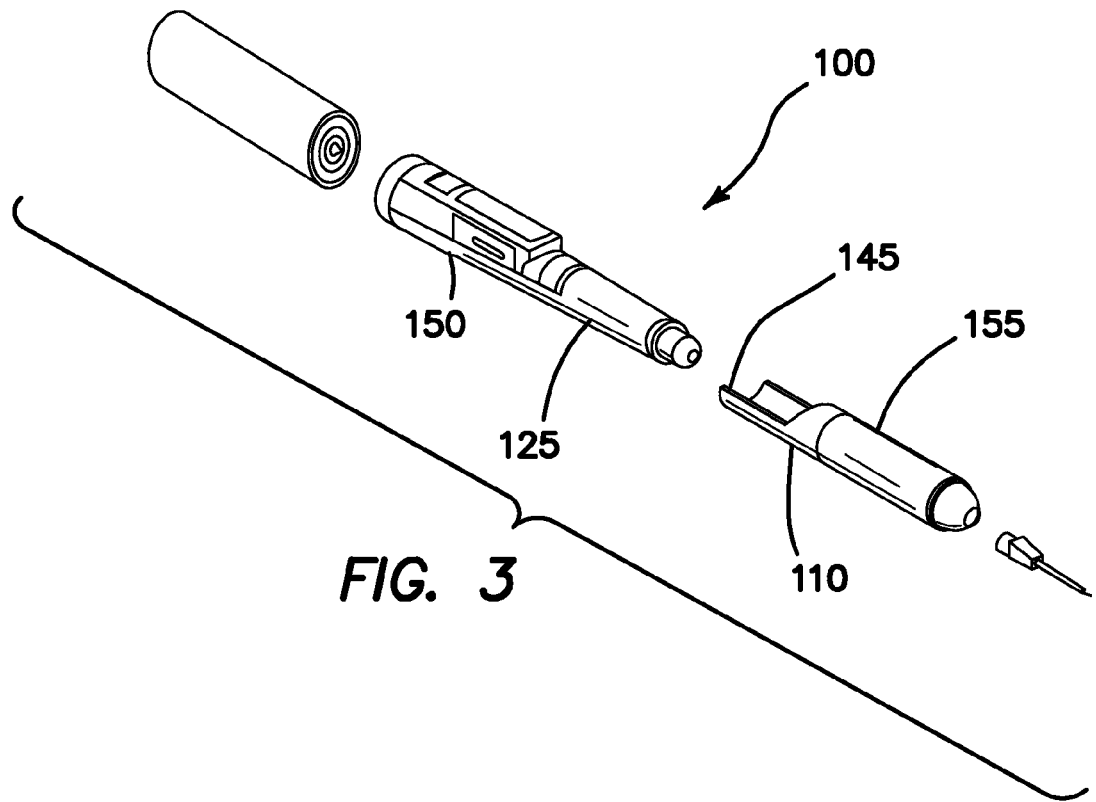
FIG. 3 is an exploded view of the medical laser handpiece of FIG. 1.

FIG. 3 is an exploded view of an embodiment of the handpiece 100 of FIGS. 1 and 2. The outer sleeve 110, including ribs (not illustrated) for tactile feeling and ease of actuation, is demonstrated to be removable in FIG. 3, thus exposing the inner sleeve 125. The internal pads 130 having conductive surfaces 135 are formed on an inner surface of the inner sleeve 125, although not shown in FIG. 3. The removable outer sleeve 110 may include an outer membrane 145, which may be formed of a silicone material. As such, the removable outer sleeve 110 may constitute an outer shell that can be removed and sterilized, e.g., in an autoclave, and replaced. An interlocking design formed by a male part 145 of the outer sleeve 110 and a female part 150 of the handpiece may act to align properly the ribs 115 on the outer sleeve 110 with the internal pads 130.

Figure 4:
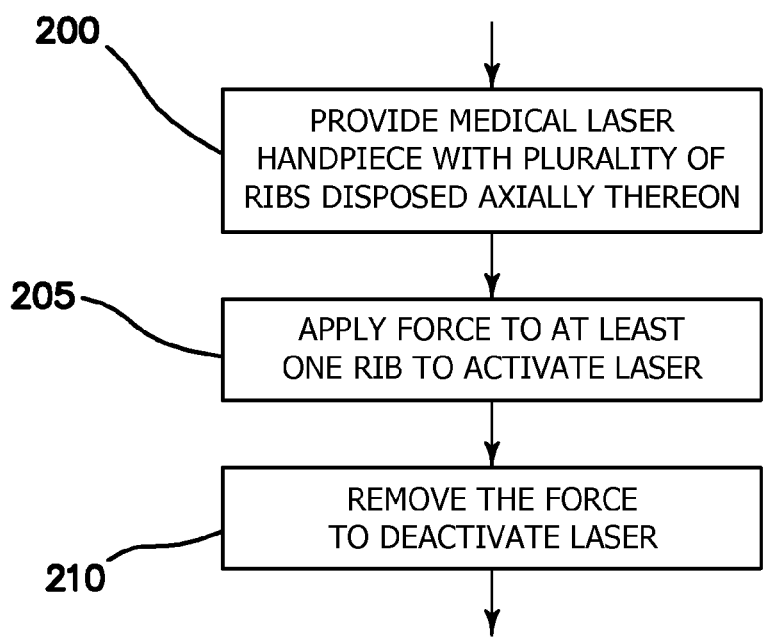
FIG. 4 is a flow diagram illustrating an implementation of a method of operating an embodiment of the present invention to control a medical device.

FIG. 4 is a flow diagram illustrating an implementation of a method of operating an embodiment of the present invention to control a medical device. The implementation commences at step 200 by providing a medical laser handpiece having a plurality of ribs disposed axially on an outer surface of the handpiece. For example, FIGS. 1, 2 and 3 present three representations of a medical laser handpiece 100 that may be provided at step 200. The laser may be activated at step 205 by applying force to at least one of the ribs. Typically, the handpiece is held in a hand of a user, whereby applying the force can be done naturally and conveniently by simply squeezing the handpiece, the shape of the handpiece and the position of the ribs fitting naturally into the hand in multiple orientations. While active, the laser can be easily moved and operated (e.g., equivalently operated) according to any appropriate medical or dental procedure without a need to change a grip on the handpiece. To deactivate the laser, the force may be removed at step 210 by relaxing the squeezing force on the handpiece. Again, it is not necessary to change the basic grip on the handpiece in order to accomplish either the activation or the deactivation of the laser.

According to one feature of the present invention, an output tip (e.g., FIG. 3) is interchangeable to allow switching between different output tips for functionality variation, such as a change of the width, composition, cross-sectional shape and/or power density of an output and/or for cleaning/autoclaving. The electromagnetic energy emitted by the handpiece may comprise laser energy and/or visible light and may operate to provide or promote one or more of cutting, ablating, desterilization, bacterial reduction, biostimulation (e.g., low-level light therapy), coagulation, remodeling, caries detection or treatment, and illumination (e.g., with visible light). In certain implementations, the electromagnetic energy can comprise one or more of an electromagnetic energy source of ablation, and/or an electromagnetic energy source of illumination, and/or an electromagnetic energy source of tissue disruption, and/or an electromagnetic energy source of biostimulation. The target surface may comprise, for example, one or more of tooth tissue, bone, cartilage and soft tissue such as skin or nasal-cavity tissue.

According to certain aspects of the present invention, the energy output can comprise one or more of hard-tissue ablating electromagnetic energy, low-level light therapy (LLLT) electromagnetic energy, tissue-biostimulation electromagnetic energy, visible electromagnetic energy, coherent light, one or more of a wavelength within a range from about 2.69 to about 2.80 microns and a wavelength of about 2.94 microns, and electromagnetic energy generated by one or more of an Er:YAG laser, an Er:YSGG laser, an Er, a Cr:YSGG laser and a CTE:YAG laser.

In one implementation, a structure (e.g., cannula(s) or orifice(s)) can be configured to direct liquid in a direction toward the distal end of the output tip. For example, a fluid can be routed distally along an outer surface (e.g., the entire or substantially the entire outer surface, near the distal end) of the output tip. In another implementation, fluid may be supplied through one or more gaps disposed between an outer surface of an electromagnetic energy waveguide (e.g., fiber optic) and the interior surface of a cannula. The fluid can be a liquid or may comprise a combination of liquid and gas. In certain implementations, the liquid is or comprises water, and in other implementations it is or comprises both air and water which, for example, can be mixed together either before or within the gap. For example, the fluid can comprise atomized fluid particles formed from a mixture of pressurized air and water and delivered through the gap to exit from the fluid output.

According to other implementations, the apparatus can comprise a fluid output that is configured to emit fluid in a vicinity of the distal end of the apparatus, wherein: the fluid output comprises an atomizer configured to place atomized fluid particles into a volume above the target surface. Further, the electromagnetic energy waveguide is configured to impart relatively large amounts of energy into the atomized fluid particles in the volume above the target surface to thereby expand the atomized fluid particles and impart disruptive forces onto the target surface.

According to another aspect of the present invention, a medical handpiece includes a handpiece housing and a source of electromagnetic energy disposed within the handpiece housing and adapted for emitting electromagnetic energy from a distal end of the handpiece housing. An illumination source is disposed within the handpiece housing for projecting light from the distal end of the handpiece housing onto a target surface. The illumination source may include a fiber optic bundle. A medication line may also be disposed within the handpiece housing for outputting medication through a distal end of the handpiece housing onto a target surface.

Any one or more of an output and/or function, such as any one or more (e.g., all) of the mentioned outputs and functions, may be independently actuatable by a corresponding one or more of the ribs. For instance, different ribs may provide different functions. In addition to and/or as an alternative to the ribs being disposed axially on the handpiece, any one or more of the ribs may be disposed radially on the handpiece. Any one or more of the ribs may contain a different shape, alignment (e.g., axial, radial, or a combination thereof) and/or texture than the others, and/or any one or more of the different shapes or textures may correspond to any one or more of the outputs or functions.

According to certain implementations, laser energy from a trunk fiber is output from a power or treatment fiber, and is directed, for example, into fluid (e.g., an air and/or water spray or an atomized distribution of fluid particles from a water connection and/or a spray connection near an output end of a handpiece) that is emitted from a fluid output of a handpiece above a target surface (e.g., one or more of tooth, bone, cartilage, and soft tissue). The fluid output may comprise a plurality of fluid outputs, concentrically arranged around a power fiber, as described in, for example, application Ser. No. 11/042,824 and Prov. App. 60/601,415. The power or treatment fiber may be coupled to an electromagnetic energy source comprising one or more of a wavelength within a range from about 2.69 to about 2.80 microns and a wavelength of about 2.94 microns. In certain implementations the power fiber may be coupled to one or more of an Er:YAG laser, an Er:YSGG laser, an Er, Cr:YSGG laser and a CTE:YAG laser, and in particular instances may be coupled to one of an Er, Cr:YSGG solid state laser having a wavelength of about 2.789 microns and an Er:YAG solid state laser having a wavelength of about 2.940 microns. An apparatus including corresponding structure for directing electromagnetic energy into an atomized distribution of fluid particles above a target surface is disclosed, for example, in the below-referenced U.S. Pat. No. 5,574,247, which describes the impartation of laser energy into fluid particles to thereby apply disruptive forces to the target surface.

By way of the disclosure herein, a laser assembly has been described that can output electromagnetic radiation useful to diagnose, monitor, and/or affect a target surface. In the case of procedures using fiber optic tip radiation, a probe can include one or more power or treatment fibers for transmitting treatment radiation to a target surface for treating (e.g., ablating) a dental structure, such as within a canal. In any of the embodiments described herein, the light for illumination and/or diagnostics may be transmitted simultaneously with, or intermittently with or separate from, transmission of treatment radiation and/or of the fluid from the fluid output or outputs.

Corresponding or related structure and methods described in the following patents assigned to Biolase Technology, Inc. are incorporated herein by reference in their entireties, wherein such incorporation includes corresponding or related structure (and modifications thereof) in the following patents which may be, in whole or in part, (i) operable with, (ii) modified by one skilled in the art to be operable with, and/or (iii) implemented/used with or in combination with, any part(s) of the present invention according to this disclosure, that of the patents or below applications, and the knowledge and judgment of one skilled in the art.

Such patents include, but are not limited to U.S. Pat. No. 7,578,622 entitled Contra-angle rotating handpiece having tactile-feedback tip ferrule; U.S. Pat. No. 7,575,381 entitled Fiber tip detector apparatus and related methods; U.S. Pat. No. 7,563,226 entitled Handpieces having illumination and laser outputs; U.S. Pat. No. 7,467,946 entitled Electromagnetic radiation emitting toothbrush and dentifrice system; U.S. Pat. No. 7,461,982 entitled Contra-angle rotating handpiece having tactile-feedback tip ferrule; U.S. Pat. No. 7,461,658 entitled Methods for treating eye conditions; U.S. Pat. No. 7,458,380 entitled Methods for treating eye conditions; U.S. Pat. No. 7,424,199 entitled Fiber tip fluid output device;

U.S. Pat. No. 7,421,186 entitled Modified-output fiber optic tips; U.S. Pat. No. 7,415,050 entitled Electromagnetic energy distributions for electromagnetically induced mechanical cutting; U.S. Pat. No. 7,384,419 entitled Tapered fused waveguide for delivering treatment electromagnetic radiation toward a target surface; U.S. Pat. No. 7,356,208 entitled Fiber detector apparatus and related methods; U.S. Pat. No. 7,320,594 entitled Fluid and laser system; U.S. Pat. No. 7,303,397 entitled Caries detection using timing differentials between excitation and return pulses; U.S. Pat. No. 7,292,759 entitled Contra-angle rotating handpiece having tactile-feedback tip ferrule; U.S. Pat. No. 7,290,940 entitled Fiber tip detector apparatus and related methods; U.S. Pat. No. 7,288,086 entitled High-efficiency, side-pumped diode laser system; U.S. Pat. No. 7,270,657 entitled Radiation emitting apparatus with spatially controllable output energy distributions; U.S. Pat. No. 7,261,558 entitled Electromagnetic radiation emitting toothbrush and dentifrice system; U.S. Pat. No. 7,194,180 entitled Fiber detector apparatus and related methods; U.S. Pat. No. 7,187,822 entitled Fiber tip fluid output device; U.S. Pat. No. 7,144,249 entitled Device for dental care and whitening; U.S. Pat. No. 7,108,693 entitled Electromagnetic energy distributions for electromagnetically induced mechanical cutting; U.S. Pat. No. 7,068,912 entitled Fiber detector apparatus and related methods; U.S. Pat. No. 6,942,658 entitled Radiation emitting apparatus with spatially controllable output energy distributions; U.S. Pat. No. 6,829,427 entitled Fiber detector apparatus and related methods; U.S. Pat. No. 6,821,272 entitled Electromagnetic energy distributions for electromagnetically induced cutting; U.S. Pat. No. 6,744,790 entitled Device for reduction of thermal lensing; U.S. Pat. No. 6,669,685 entitled Tissue remover and method; U.S. Pat. No. 6,616,451 entitled Electromagnetic radiation emitting toothbrush and dentifrice system; U.S. Pat. No. 6,616,447 entitled Device for dental care and whitening; U.S. Pat. No. 6,610,053 entitled Methods of using atomized particles for electromagnetically induced cutting; U.S. Pat. No. 6,567,582 entitled Fiber tip fluid output device; U.S. Pat. No. 6,561,803 entitled Fluid conditioning system; U.S. Pat. No. 6,544,256 entitled Electromagnetically induced cutting with atomized fluid particles for dermatological applications; U.S. Pat. No. 6,533,775 entitled Light-activated hair treatment and removal device; U.S. Pat. No. 6,389,193 entitled Rotating handpiece; U.S. Pat. No. 6,350,123 entitled Fluid conditioning system; U.S. Pat. No. 6,288,499 entitled Electromagnetic energy distributions for electromagnetically induced mechanical cutting; U.S. Pat. No. 6,254,597 entitled Tissue remover and method; U.S. Pat. No. 6,231,567 entitled Material remover and method; U.S. Pat. No. 6,086,367 entitled Dental and medical procedures employing laser radiation; U.S. Pat. No. 5,968,037 entitled User programmable combination of atomized particles for electromagnetically induced cutting; U.S. Pat. No. 5,785,521 entitled Fluid conditioning system; and U.S. Pat. No. 5,741,247 entitled Atomized fluid particles for electromagnetically induced cutting.

Also, the above disclosure and referenced items, and that described on the referenced pages, are intended to be operable or modifiable to be operable, in whole or in part, with corresponding or related structure and methods, in whole or in part, described in the following published applications and items referenced therein, which applications are listed as follows: App. Pub. 20090225060 entitled Wrist-mounted laser with animated, page-based graphical user-interface; App. Pub. 20090143775 entitled Medical laser having controlled-temperature and sterilized fluid output; App. Pub. 20090141752 entitled Dual pulse-width medical laser with presets; App. Pub. 20090105707 entitled Drill and flavored fluid particles combination; App. Pub. 20090104580 entitled Fluid and pulsed energy output system; App. Pub. 20090076490 entitled Fiber tip fluid output device; App. Pub. 20090075229 entitled Probes and biofluids for treating and removing deposits from tissue surfaces; App. Pub. 20090067189 entitled Contra-angle rotating handpiece having tactile-feedback tip ferrule; App. Pub. 20090062779 entitled Methods for treating eye conditions with low-level light therapy; App. Pub. 20090056044 entitled Electromagnetic radiation emitting toothbrush and dentifrice system; App. Pub. 20090043364 entitled Electromagnetic energy distributions for Electromagnetically induced mechanical cutting; App. Pub. 20090042171 entitled Fluid controllable laser endodontic cleaning and disinfecting system; App. Pub. 20090035717 entitled Electromagnetic radiation emitting toothbrush and transparent dentifrice system; App. Pub. 20090031515 entitled Transparent dentifrice for use with electromagnetic radiation emitting toothbrush system; App. Pub. 20080317429 entitled Modified-output fiber optic tips; App. Pub. 20080276192 entitled Method and apparatus for controlling an electromagnetic energy output system; App. Pub. 20080240172 entitled Radiation emitting apparatus with spatially controllable output energy distributions; App. Pub. 20080221558 entitled Multiple fiber-type tissue treatment device and related method; App. Pub. 20080219629 entitled Modified-output fiber optic tips; App. Pub. 20080212624 entitled Dual pulse-width medical laser; App. Pub. 20080203280 entitled Target-close electromagnetic energy emitting device; App. Pub. 20080181278 entitled Electromagnetic energy output system; App. Pub. 20080181261 entitled Electromagnetic energy output system; App. Pub. 20080157690 entitled Electromagnetic energy distributions for electromagnetically induced mechanical cutting; App. Pub. 20080151953 entitled Electromagnet energy distributions for electromagnetically induced mechanical cutting; App. Pub. 20080138764 entitled Fluid and laser system; App. Pub. 20080125677 entitled Methods for treating hyperopia and presbyopia via laser tunneling; App. Pub. 20080125676 entitled Methods for treating hyperopia and presbyopia via laser tunneling; App. Pub. 20080097418 entitled Methods for treating eye conditions; App. Pub. 20080097417 entitled Methods for treating eye conditions; App. Pub. 20080097416 entitled Methods for treating eye conditions; App. Pub. 20080070185 entitled Caries detection using timing differentials between excitation and return pulses; App. Pub. 20080069172 entitled Electromagnetic energy distributions for electromagnetically induced mechanical cutting; App. Pub. 20080065057 entitled High-efficiency, side-pumped diode laser system; App. Pub. 20080065055 entitled Methods for treating eye conditions; App. Pub. 20080065054 entitled Methods for treating hyperopia and presbyopia via laser tunneling; App. Pub. 20080065053 entitled Methods for treating eye conditions; App. Pub. 20080033411 entitled High efficiency electromagnetic laser energy cutting device; App. Pub. 20080033409 entitled Methods for treating eye conditions; App. Pub. 20080033407 entitled Methods for treating eye conditions; App. Pub. 20080025675 entitled Fiber tip detector apparatus and related methods; App. Pub. 20080025672 entitled Contra-angle rotating handpiece having tactile-feedback tip ferrule; App. Pub. 20080025671 entitled Contra-angle rotating handpiece having tactile-feedback tip ferrule; App. Pub. 20070298369 entitled Electromagnetic radiation emitting toothbrush and dentifrice system; App. Pub. 20070263975 entitled Modified-output fiber optic tips; App. Pub. 20070258693 entitled Fiber detector apparatus and related methods; App. Pub. 20070208404 entitled Tissue treatment device and method; App. Pub. 20070208328 entitled Contra-angel rotating handpiece having tactile-feedback tip ferrule; App. Pub. 20070190482 entitled Fluid conditioning system; App. Pub. 20070184402 entitled Caries detection using real-time imaging and multiple excitation frequencies; App. Pub. 20070128576 entitled Output attachments coded for use with electromagnetic-energy procedural device; App. Pub. 20070104419 entitled Fiber tip fluid output device; App. Pub. 20070060917 entitled High-efficiency, side-pumped diode laser system; App. Pub. 20070059660 entitled Device for dental care and whitening; App. Pub. 20070054236 entitled Device for dental care and whitening; App. Pub. 20070054235 entitled Device for dental care and whitening; App. Pub. 20070054233 entitled Device for dental care and whitening; App. Pub. 20070042315 entitled Visual feedback implements for electromagnetic energy output devices; App. Pub. 20070016176 entitled Laser handpiece architecture and methods; App. Pub. 20070014517 entitled Electromagnetic energy emitting device with increased spot size; App. Pub. 20070014322 entitled Electromagnetic energy distributions for electromagnetically induced mechanical cutting; App. Pub. 20070009856 entitled Device having activated textured surfaces for treating oral tissue; App. Pub. 20070003604 entitled Tissue coverings bearing customized tissue images; App. Pub. 20060281042 entitled Electromagnetic radiation emitting toothbrush and dentifrice system; App. Pub. 20060275016 entitled Contra-angle rotating handpiece having tactile-feedback tip ferrule; App. Pub. 20060241574 entitled Electromagnetic energy distributions for electromagnetically induced disruptive cutting; App. Pub. 20060240381 entitled Fluid conditioning system; App. Pub. 20060210228 entitled Fiber detector apparatus and related methods; App. Pub. 20060204203 entitled Radiation emitting apparatus with spatially controllable output energy distributions; App. Pub. 20060142745 entitled Dual pulse-width medical laser with presets; App. Pub. 20060142744 entitled Identification connector for a medical laser handpiece; App. Pub. 20060142743 entitled Medical laser having controlled-temperature and sterilized fluid output; App. Pub. 20060126680 entitled Dual pulse-width medical laser; App. Pub. 20060099548 entitled Caries detection using timing differentials between excitation and return pulses; App. Pub. 20060083466 entitled Fiber tip detector apparatus and related methods; App. Pub. 20060043903 entitled Electromagnetic energy distributions for electromagnetically induced mechanical cutting; App. Pub. 20050283143 entitled Tissue remover and method; App. Pub. 20050281887 entitled Fluid conditioning system; App. Pub. 20050281530 entitled Modified-output fiber optic tips; App. Pub. 20050256517 entitled Electromagnetically induced treatment devices and methods; App. Pub. 20050256516 entitled Illumination device and related methods; App. Pub. 20040106082 entitled Device for dental care and whitening; App. Pub. 20040092925 entitled Methods of using atomized particles for electromagnetically induced cutting; App. Pub. 20040091834 entitled Electromagnetic radiation emitting toothbrush and dentifrice system; App. Pub. 20040068256 entitled Tissue remover and method; App. Pub. 20030228094 entitled Fiber tip fluid output device; App. Pub. 20020149324 entitled Electromagnetic energy distributions for electromagnetically induced mechanical cutting; and App. Pub. 20020014855 entitled Electromagnetic energy distributions for electromagnetically induced mechanical cutting.

All of the contents of the preceding applications are incorporated herein by reference in their entireties. Although the disclosure herein refers to certain illustrated embodiments, it is to be understood that these embodiments have been presented by way of example rather than limitation. For example, any of the radiation outputs (e.g., lasers), any of the fluid outputs (e.g., water outputs), and any conditioning agents, particles, agents, etc., and particulars or features thereof, or other features, including method steps and techniques, may be used with any other structure(s) and process described or referenced herein, in whole or in part, in any combination or permutation as a non-equivalent, separate, non-interchangeable aspect of this invention. Corresponding or related structure and methods specifically contemplated, disclosed and claimed herein as part of this invention, to the extent not mutually inconsistent as will be apparent from the context, this specification, and the knowledge of one skilled in the art, including, modifications thereto, which may be, in whole or in part, (i) operable and/or constructed with, (ii) modified by one skilled in the art to be operable and/or constructed with, and/or (iii) implemented/made/used with or in combination with, any parts of the present invention according to this disclosure, include: (I) any one or more parts of the above disclosed or referenced structure and methods and/or (II) subject matter of any one or more of the following claims and parts thereof, in any permutation and/or combination. The intent accompanying this disclosure is to have such embodiments construed in conjunction with the knowledge of one skilled in the art to cover all modifications, variations, combinations, permutations, omissions, substitutions, alternatives, and equivalents of the embodiments, to the extent not mutually exclusive, as may fall within the spirit and scope of the invention as limited only by the appended claims.

What is claimed is:

1. A medical instrument comprising:
a cylindrical handpiece;
an electrical circuit for actuating a medical laser, the circuit including axially elongated contact strips at circumferentially spaced-apart locations within the handpiece;
axially elongated pads in radial alignment with the contact strips and configured to actuate the circuit when pressed against the contact strips; and
axially elongated ribs located at the outer circumference of the handpiece in radial alignment with the pads, the ribs being manually movable radially inward against the pads to press the pads against the contact strips and thereby to actuate the circuit.

2. A medical instrument as defined in claim 1 further comprising axially elongated plungers projecting radially inward from the ribs to press the pads against the contact strips when the ribs are moved radially inward.

3. A medical instrument as defined in claim 2 wherein the ribs are resiliently deflectable radially inward from rest positions in which the plungers are spaced radially outward from the pads.

4. A medical instrument as defined in claim 2 wherein the ribs and plungers are portions of a resiliently deflectable sleeve extending circumferentially and axially over the contact strips and the pads.

* * * * *